United States Patent
Hakim

(10) Patent No.: US 9,949,920 B2
(45) Date of Patent: *Apr. 24, 2018

(54) ROLL ON NATURAL DEODORANT AND METHOD OF USE

(71) Applicant: Noha N. Hakim, Easton, PA (US)

(72) Inventor: Noha N. Hakim, Easton, PA (US)

( * ) Notice: Subject to any disclaimer, the term of this patent is extended or adjusted under 35 U.S.C. 154(b) by 90 days.

This patent is subject to a terminal disclaimer.

(21) Appl. No.: 15/159,482

(22) Filed: May 19, 2016

(65) Prior Publication Data
US 2017/0333336 A1    Nov. 23, 2017

(51) Int. Cl.
| | | |
|---|---|---|
| A61K 8/00 | (2006.01) | |
| A61K 8/97 | (2017.01) | |
| A61Q 15/00 | (2006.01) | |
| A61K 8/92 | (2006.01) | |
| A61K 8/37 | (2006.01) | |
| A61K 8/34 | (2006.01) | |

(52) U.S. Cl.
CPC .................. *A61K 8/97* (2013.01); *A61K 8/34* (2013.01); *A61K 8/375* (2013.01); *A61K 8/92* (2013.01); *A61Q 15/00* (2013.01); *A61K 2800/524* (2013.01); *A61K 2800/596* (2013.01)

(58) Field of Classification Search
CPC ...... A61K 2300/00; A61K 8/97; A61K 36/67; A61K 36/81; A61K 2800/524; A61K 2800/596; A61K 31/4155; A61K 8/20; A61K 8/36; A61K 8/375; A61K 8/732; A61K 8/92; A61K 8/922; A61Q 15/00; A61Q 19/007; A61Q 17/04; A61Q 19/00; A61Q 19/005; A61Q 19/08
See application file for complete search history.

(56) References Cited

U.S. PATENT DOCUMENTS

| | | | | |
|---|---|---|---|---|
| 4,505,902 A | * | 3/1985 | Millard | A61K 8/922 424/735 |
| 4,943,432 A | * | 7/1990 | Biener | A61K 8/19 424/647 |
| 5,705,172 A | * | 1/1998 | Efron | A61F 7/02 424/402 |
| 5,866,145 A | * | 2/1999 | Stavroff | A61K 8/03 424/401 |
| 6,582,709 B1 | * | 6/2003 | Maor | A61K 8/27 424/401 |
| 6,723,309 B1 | * | 4/2004 | Deane | A61K 8/416 424/70.1 |
| 8,486,463 B1 | * | 7/2013 | Brieva | A61K 8/97 424/725 |
| 2006/0134238 A1 | * | 6/2006 | Dnyaneshwar | A61K 36/886 424/744 |
| 2008/0175928 A1 | * | 7/2008 | Jochim | A61K 8/0212 424/727 |
| 2008/0286390 A1 | * | 11/2008 | Tanyi | A61K 8/922 424/744 |
| 2011/0212184 A1 | * | 9/2011 | Samelson | A61K 8/044 424/537 |

* cited by examiner

*Primary Examiner* — Nannette Holloman
(74) *Attorney, Agent, or Firm* — Gary P. Topolosky

(57) ABSTRACT

This invention is a natural deodorant composition that exploits the benefits of Dead Sea salt by adding it to a base of organic *aloe vera* juice, organic coconut oil, sweet almond oil, olive oil, NF emulsified wax (vegetable based), potato starch, and apple cider vinegar. It also includes several 100% pure essential oils, and preservatives.

14 Claims, No Drawings

ROLL ON NATURAL DEODORANT AND METHOD OF USE

HISTORY

Many antiperspirants contain aluminum that has been implicated as a risk factor for both breast cancer and Alzheimer's disease. Therefore, it is beneficial to control the body odor without the use of aluminum.

Most skincare products use heavily synthetic preservatives (such as parabens and triclosan) to increase shelf life to 2-3 years. However, all synthetic preservatives may be considered toxic in high doses and cause skin irritation and allergies, particularly on sensitive skins.

Therefore, it would be better to use natural preservatives with little amount of synthetic preservatives to control all kinds of bacteria, fungi and molds to assure the safety of the products.

Other chemicals used in skincare products as stabilizers or emulsified agents such as phthalates that may cause breast cancer. It is better to use emulsified wax (vegetable base) that conforms to the current USP/NF Monograph.

Lecithin, derived from soy, and gluten are used in the formulation of some cosmetics and personal care products due to their ability to form emulsions. Skin care products with lecithin and gluten may cause allergic reactions.

FIELD OF THE INVENTION

This invention relates to deodorants for use by humans. Particularly, it relates to a natural deodorant for applying to the underarms via roll-on bottles. Preferred compositions, currently sold under the SeaLand Cosmetics™ brand.

The SeaLand Cosmetics Natural Deodorant is a combination of the earth's natural ingredients and 6% of Dead Sea salt to clean, hydrate and prevent odor by balancing the pH of the skin at its normal acid mantle pH (4.5-6) with a combination of the natural preservative Leucidal liquid (plant-based) and phenoxyethanol which is a nature identical chemical that can be found in green tea and produced by treating phenol with ethylene oxide in an alkaline medium that reacts to form a pH balanced ingredient. This synthetically produced commercial ingredient fights bacteria and doesn't release formaldelyde or cause health risks and assures the safety of the product. One commercial product is Optiphen® Plus and it is used with <1.0% in the deodorant formulations of this invention. Should Optiphen no longer be commercially available, substantially equivalent alternatives may be substituted therefor.

BACKGROUND OF THE INVENTION

Dead Sea salt, as removed from waters from the Dead Sea water, is a known component for various preferred end uses.

Biener U.S. Pat. No. 4,943,432 added such salts to magnesium halide, several alkaline earth metal salts and other cations as part of a composition for treating psoriasis.

Stravroff et al. U.S. Pat. No. 5,866,145 mixed Dead Sea salts with some silicone oils and fragrances to serve as a moisturizing body "polisher".

Maor et al. U.S. Pat. No. 6,582,709 discloses a pharmaceutical cream composition for the treatment of skin disorders, said composition including about 1-6 wt. % Dead Sea mud as an active ingredient.

Lucenta U.S. Published Application No. 20110229419 mixed Dead Sea salt with sodium chloride for the prevention and healing of canker sores.

And Samuelson et al. U.S. Pat. No. 9,050,273 discloses using ultra fine Dead Sea mineral compounds in compositions for use in bath and body products.

Two other particularly pertinent references to natural deodorants include the herbal composition in Levin U.S. Pat. No. 6,436,415 and the topical composition of Gorman U.S. Pat. No. 7,736,632.

The Dead Sea is one of the most saline lakes in the world. It lies between the hills of Judaea to the west and the Trans-Jordanian plateaus to the east. The Jordan River flows from the north into the Dead Sea. About 2.5 million years ago, heavy stream flow into the lake deposited thick sediments containing shale, clay, sandstone, rock salt, and gypsum. After this, strata of clay, marl, soft chalk, and gypsum fell upon layers of sand and gravel.

Having no outlet, the Dead Sea is a "terminal lake" meaning that it loses huge amounts of water by evaporation in the hot dry air. The water has evaporated faster than it has been replenished by precipitation over the last 10,000 years. That results in the lake gradually shrinking to its present form. Because of this, bare deposits cover the Dead Sea valley to a thickness of 1 to 4 miles (1.6 to 6.4 km). This water evaporation has also resulted in high concentrations of salts and minerals in a unique composition particularly rich in magnesium, sodium, potassium, calcium, bromide and various other minor anions such as, e.g., sulfate.

The concentration of salt increases as one descends toward the bottom of the Dead Sea. Down to 130 feet (40 m), the temperature varies from 66 to 98° F. (19 to 37° C.), and the salinity is slightly less than 300 parts per thousand. At this depth, the water is particularly rich in sulfates and bicarbonates. There is a transition zone located between 130 and 330 feet (40 and 100 m). The lower waters below 330 ft (100 m) have a uniform temperature of about 72° F. (22° C.) and a higher degree of salinity (approximately 332 parts per thousand). This lower water contains hydrogen sulfide along with strong concentrations of magnesium, potassium, chlorine, and bromine. Below that level, the deepest waters are saturated with sodium chloride that precipitates to the bottom.

The lower waters of the Dead Sea are fossilized; they remain permanently on the bottom because they are very salty and dense. The upper waters date from a few centuries A.D.

The Dead Sea's mineral composition differs from that of ocean water, the salt in most oceans is approximately 85% sodium chloride while Dead Sea salt is only 12-18% sodium chloride. An analysis of major ion concentrations in the water of the Dead Sea gave the following results. (Reference 1)

The major ions in Dead Sea water are:

| Ion | Concentration (mg/L) |
| --- | --- |
| Chloride and Bromide | 230,400 |
| Magnesium | 45,900 |
| Sodium | 36,600 |
| Calcium | 17,600 |
| Potassium | 7,800 |

The Dead Sea's overall salt concentration is 340 g/L according to Reference 1. One study concluded that the high concentration of Mg in Dead Sea salt made it instrumental in improving skin hydration and reducing inflammation (Reference 2). According to Reference 3, the high concentration of bromide and magnesium in Dead Sea salt can cleanse and detoxify the skin and body. References 4 and 5 both address bathing in a Mg-rich, Dead Sea salt solution.

REFERENCES

1. Kuehl B L, Fyfe K S, Shear N H (March 2003). "*Cutaneous cleansers*". Skin Therapy Lett 8 (3): 1-4. PMID 12858234.

2. Pierce J D Jr, Zeng X N, Aronov E V, Preti G, Wysocki C J (August 1995). "*Cross-adaptation of sweaty-smelling 3-methyl-2-hexenoic acid by a structurally similar, pleasant-smelling odorant*". Chem Senses 20 (4): 401-11. doi: 10.1093/chemse/20.4.401. PMID 8590025.

3. Ma'or, Zeev et al. "*Antimicrobial properties of Dead Sea black mineral mud*", International Journal of Dermatology, May 2006. Retrieved on 2008 Apr. 13.

4. Proksch, Ehrhardt M D, PhD et al. "*Bathing in a magnesium-rich Dead Sea salt solution improves skin barrier function, enhances skin hydration, and reduces inflammation in atopic dry skin*", International Journal of Dermatology, February 2005. Retrieved on 2008 Apr. 13.

5. Ehrhardt, Proksch; Nissen, H P; Bremgartner, M; Urquhart, C. "*Bathing in a magnesium-rich Dead Sea salt solution: follow-on review*". International Journal of Dermatology 46 (2): 177-179. doi:10.1111/j.1365-4632.2005.02079.x. PMID 15689218.

SUMMARY OF THE INVENTION

A first object of the invention is to create a natural formulation that contains Dead Sea salt for humans to use as an underarm (roll on) deodorant.

A second object is to create a pH-balanced deodorant formulation by including natural ingredients such as organic *aloe Vera* juice, organic coconut oil, sweet almond oil, apple cider vinegar and pure essential oils such as sage, eucalyptus and tea tree to work in harmony for neutralizing odor and help to moisturize the human skin in the armpit regions.

A third object is to assure that this deodorant formulation contains no aluminum, no parabens, no phthalates, no triclosan, no soy and no gluten.

A fourth object is to assure that this natural deodorant is non-oily, non-staining and absorbed quickly with no residue on skin.

A fifth object is to assure the safety of the product by adding natural plant based preservative (Leucidal liquid) and phenoxyethanol (Optiphen® Plus, the listed ingredients of which include phenoxyethanol, caprylyl glycol and sorbic acid). Also natural preservatives included in the organic *aloe vera* juice (potassium sorbate and citric acid).

DESCRIPTION OF PREFERRED EMBODIMENTS

Ideally, the composition of this deodorant includes the following in addition to its main novel ingredient of Dead Sea salt.

*Aloe vera* Juice:

It is used instead of water as a diluent; it soothes the skin and helps replenish its moisture.

Organic Coconut Oil:

Coconut oil has wide benefits to skin and hair. It is a moisturizer for all types of skin. It contains lauric acid which gives it antibacterial and antiviral properties that help to prevent sweat odor.

Olive Oil:

Olive oil is composed mainly of the mixed triglyceride esters of Oleic and palmitic acids and other fatty acids. It contains three major antioxidants: vitamin E, polyphenols, and phytosterols to help to calm irritation and act as gentle moisturizer for dry skin. Also when olive oil blends well with coconut oil before adding it to the formula, it decreases the chance of the organic coconut oil to convert back to its solid state in cold environment.

Sweet Almond Oil

It is included for its high content of vitamin E and D It is also rich in oleic and linoleic acids and absorbed quickly by the skin.

NF Emulsifying Wax (Vegetable Based):

It is used to form emulsion between water and oil ingredients by attracting them to different portions of its structure (hydrophilic for water molecules and hydrophobic for oil molecules).

Apple Cider Vinegar:

It keeps the pH of the deodorant formula at the acidic side and helps to neutralize bad smells.

Potato Starch:

It is added for thickening the lotion and add a soft touch to the lotion.

Preservatives:

One preferred set of preservatives for use in this product consists of:

(i) 1.2% natural preservative called Leucidal Liquid, it is a product derived from radishes fermented with *Leuconostoc kimchii*, a lactic acid bacteria that has traditionally been used to make kimchi, this product consists of an isolated peptide that is secreted from the bacteria during the fermentation process that has been shown to have antimicrobial benefits. Leucidal® Liquid is accepted by ECOcert as an ingredient in certified organic cosmetics.

and (ii) 0.8% Phenoxyethanol. Though the latter is not natural, it is the only synthetic preservative which: doesn't release formaldehyde, works well with formulas having a pH less than 6 and which causes the least (i) skin irritation. One representative off-the-shelf preservative is a product called Optiphen® Plus, the listed ingredients of which include phenoxyethanol, caprylyl glycol and sorbic acid.

Pure Essential Oils:

There is a preferred combination of essential present in every variety of this natural deodorant. Sage is added because it helps to evaporate the moisture on the skin and decrease body odor. Eucalyptus is included because of its anti-inflammatory and deodorant properties. And tea tree has antibacterial and antiseptic activities.

If the desired end product is meant to be scent free, the preceding list of additives is complete. Should the user/consumer desire some natural scents, however, variations can be made and sold to provide a non-overpowering hint of one of the following: anise, lemongrass, peppermint, tangerine and bergamot, lavender or palmarosa.

Example

The roll-on deodorant container is 3 oz. in size with about 2.7 oz. of fluid deodorant included therein. A main formula of that fluid according to this invention consists of:

60 wt. % *aloe vera* juice (whole leaf), organic 13 wt. % organic coconut oil 6 wt. % Dead Sea salt (or roughly 30 g by wt. in a 500 g batch)

6 wt. % olive oil
5 wt. % sweet almond oil
4 wt. % NF emulsified wax (vegetable based)
2 wt. % potato starch
1 wt. % apple Cider vinegar
1 wt. % pure essential oils (sage, eucalyptus and tea tree) plus a specific fourth oil ingredient for making this deodorant into 1 of 7 different kinds:
  1. natural scent (nothing else added), or scented with: (2. anise, 3. lemongrass, 4. peppermint, 5. tangerine and bergamot, 6. lavender or 7. palmarosa).
2 wt. % of a preservative, consisting of: 1.2% Leucidal liquid and 0.8% phenoxethanol (Optiphen Plus)

It should be noted that the organic *Aloe vera* juice used in this formula contains natural preservatives, particularly potassium sorbate and citric acid.

Preferred embodiments of this deodorant offer a pH-balanced formula (accomplished by adding together apple cider vinegar, sweet almond oil and the pure essential oils). The aforesaid combination of components achieves a pH in the range of about 3-5. The natural acid environment of the skin will provide suitable environment for good bacteria to grow while killing other microorganisms that is the reason of the sweat odor that the formula of this invention will neutralize.

The aforementioned ingredients are mixed altogether and bottled in a roll-on style dispenser. Directions for use of this invention are as follows:

First shake the container/bottle before applying to just the user's armpits after they have been cleaned and dried. Note that a temporary burning sensation may occur when applied directly after that area has been recently shaven due to the presence of apple cider vinegar in this formula.

Needless to say, keep the container tightly closed when not in use.

If the user suspects an allergic reaction, he/she should discontinue further uses and consult a physician. Allergic reactions should be minimized, however, since (unlike many other deodorant and/or skin care products on the shelves, this invention contains no aluminum, no parabens, no phthalates, no triclosan, no soy and no gluten.

Certain pharmacologically accepted ingredients normally found in some known deodorants may also be added to the instant roll on formulation though on a less preferred basis.

While the invention has been described with a certain degree of particularity, it is manifest that many changes may be made in the arrangement of components without departing from the spirit and scope of this disclosure. It is understood that the invention is not limited to the embodiments set forth herein for purposes of exemplification, but is to be limited only by the scope of the attached claim or claims.

What is claimed is:

1. A deodorant for use on skin beneath a human armpit, a composition for said deodorant comprising:
   (a) about 55-65% by weight of the composition *aloe vera* juice,
   (b) about 10-16% by weight of the composition coconut oil,
   (c) about 4 to 8% by weight of the composition Dead Sea salt,
   (d) about 4 to 8% by weight of the composition olive oil,
   (e) about 3-7% by weight of the composition sweet almond oil,
   (f) about 3-5% by weight of the composition emulsified wax,
   (g) about 1-3% by weight of the composition potato starch,
   (h) about 0.5-1.5% by weight of the composition apple cider vinegar, and
   (i) about 0.5-1.5% by weight of the composition pure essential oils.

2. The deodorant of claim 1, wherein said composition further includes:
   (j) about 1.5-2.5% by weight of the composition of a preservative.

3. The deodorant of claim 2 wherein the preservative consists essentially of:
   (i) about 1.0 to 1.5% by weight of the composition of a *leuconostoc*/radish root ferment filtrate; and
   (ii) about 0.5 to 1.0% by weight of the composition phenoxyethanol.

4. The deodorant of claim 3 wherein the preservative consists essentially of:
   (i) about 1.2% by weight of the composition of the *leuconostoc*/radish root ferment filtrate; and
   (ii) about 0.8% by weight of the composition phenoxyethanol.

5. The deodorant of claim 1 wherein the pure essential oils include sage, eucalyptus and tea tree.

6. The deodorant of claim 1 wherein the pure essential oils further include a scent selected from the group consisting of: anise, lemongrass, peppermint, tangerine with bergamot, lavender and palmarosa.

7. The deodorant of claim 1 wherein said composition comprises:
   (a) about 60% by weight of the composition *aloe vera* juice,
   (b) about 13% by weight of the composition coconut oil,
   (c) about 6% by weight of the composition Dead Sea salt,
   (d) about 6% by weight of the composition olive oil,
   (e) about 5% by weight of the composition sweet almond oil,
   (f) about 4% by weight of the composition emulsified wax,
   (g) about 2% by weight of the composition potato starch,
   (h) about 1% by weight of the composition apple cider vinegar, and
   (i) about 1% by weight of the composition pure essential oils.

8. The deodorant of claim 1 wherein the pH of the composition is 4.0+/−1.0.

9. A deodorant for rolling onto skin beneath a human armpit, a composition for said deodorant comprising:
   (a) about 55-65% by weight of the composition *aloe vera* juice,
   (b) about 10-16% by weight of the composition coconut oil,
   (c) about 4 to 8% by weight of the composition Dead Sea salt,
   (d) about 4 to 8% by weight of the composition olive oil,
   (e) about 3-7% by weight of the composition sweet almond oil,
   (f) about 3-5% by weight of the composition emulsified wax,
   (g) about 1-3% by weight of the composition potato starch,
   (h) about 0.5-1.5% by weight of the composition apple cider vinegar,
   (i) about 0.5-1.5% by weight of the composition pure essential oils that includes sage, eucalyptus and tea tree; and one or more scented oils; and (j) about 1.5-2.5% by weight of the composition of preservatives.

10. The deodorant of claim 9 wherein the preservative consists essentially of:
 (i) about 1.0 to 1.5% by weight of the composition of a *leuconostoc*/radish root ferment filtrate; and
 (ii) about 0.5 to 1.0% by weight of the composition phenoxyethanol.

11. The deodorant of claim 9 wherein the one or more scented oils is selected from the group consisting of: anise, lemongrass, peppermint, tangerine & bergamot, lavender and palmarosa.

12. A method of delivering deodorant performance to an underarm area of a human comprises:
 providing a composition for delivery to the underarm area of the human, said composition comprising:
 (a) about 55-65% by weight of the composition *aloe vera* juice,
 (b) about 10-16% by weight of the composition coconut oil,
 (c) about 4 to 8% by weight of the composition Dead Sea salt,
 (d) about 4 to 8% by weight of the composition olive oil,
 (e) about 3-7% by weight of the composition sweet almond oil,
 (f) about 3-5% by weight of the composition emulsified wax,
 (g) about 1-3% by weight of the composition potato starch,
 (h) about 0.5-1.5% by weight of the composition apple cider vinegar,
 (i) about 0.5-1.5% by weight of the composition pure essential oils that includes sage, eucalyptus and tea tree; and one or more scented oils; and
 (j) about 1.5-2.5% by weight of the composition of preservatives.

13. The method of claim 12 wherein the preservative in the composition consists essentially of:
 about 1.0 to 1.5% by weight of the composition of a *leuconostoc*/radish root ferment filtrate; and about 0.5 to 1.0% by weight of the composition phenoxyethanol.

14. The method of claim 12 wherein the one or more scented oils is selected from the group consisting of: anise, lemongrass, peppermint, tangerine & bergamot, lavender and palmarosa.

\* \* \* \* \*